(12) United States Patent
Lee et al.

(10) Patent No.: US 9,701,942 B2
(45) Date of Patent: Jul. 11, 2017

(54) COMPOSITION FOR MATURING DENDRITIC CELLS, AND METHOD FOR PREPARING ANTIGEN-SPECIFIC DENDRITIC CELLS USING SAME

(71) Applicant: JW CREAGENE INC., Seongnam-si, Gyeonggi-do (KR)

(72) Inventors: Yoon Lee, Yongin-si (KR); Hye-Won Kang, Seongnam-si (KR); Seung-Soo Han, Gwangju-si (KR); Young-Mok Kim, Seoul (KR); Yong-Soo Bae, Suwon-si (KR); Seo-Hee Ahn, Gwangju-si (KR)

(73) Assignee: JW CREAGENE INC., Seongnam-si (KR)

( * ) Notice: Subject to any disclaimer, the term of this patent is extended or adjusted under 35 U.S.C. 154(b) by 130 days.

(21) Appl. No.: 14/403,878

(22) PCT Filed: May 30, 2013

(86) PCT No.: PCT/KR2013/004750
§ 371 (c)(1),
(2) Date: Nov. 25, 2014

(87) PCT Pub. No.: WO2013/180481
PCT Pub. Date: Dec. 5, 2013

(65) Prior Publication Data
US 2015/0125956 A1 May 7, 2015

(30) Foreign Application Priority Data
May 31, 2012 (KR) ........................ 10-2012-0058835

(51) Int. Cl.
*C12N 5/0784* (2010.01)
*A61K 39/00* (2006.01)

(52) U.S. Cl.
CPC .... *C12N 5/0639* (2013.01); *A61K 2039/5154* (2013.01); *C12N 2500/72* (2013.01); *C12N 2501/02* (2013.01); *C12N 2501/05* (2013.01); *C12N 2501/056* (2013.01); *C12N 2501/2301* (2013.01); *C12N 2501/2306* (2013.01); *C12N 2501/24* (2013.01); *C12N 2501/25* (2013.01); *C12N 2501/999* (2013.01); *C12N 2506/11* (2013.01)

(58) Field of Classification Search
CPC .............. C12N 5/0639; C12N 2500/72; C12N 2501/02; C12N 2501/05; C12N 2501/056; C12N 2501/2301; C12N 2501/2306; C12N 2501/24; C12N 2501/25; C12N 2501/999; C12N 2506/11; A61K 2039/5154
See application file for complete search history.

(56) References Cited

U.S. PATENT DOCUMENTS

| 8,153,425 B2 | 4/2012 | Pogue-Caley et al. |
| 2006/0269526 A1 | 11/2006 | Galipeau et al. |
| 2009/0053251 A1 | 2/2009 | Pogue-Caley et al. |
| 2012/0114680 A1 | 5/2012 | Pogue-Caley et al. |

FOREIGN PATENT DOCUMENTS

| EP | 1 959 007 A1 | 8/2008 |
| KR | 10-2003-0070454 A | 8/2003 |
| KR | 10-2010-0109099 A | 10/2010 |
| KR | 10-2011-0035633 A | 4/2011 |
| KR | 10-2011-0139363 A | 12/2011 |
| WO | 03/022215 A2 | 3/2003 |
| WO | 2006-127150 A2 | 11/2006 |

OTHER PUBLICATIONS

Ojima et al., Streptococcal preparation OK-432 promotes the capacity of dendritic cells (DCs) to prime carcinoembryonic antigen (CEA)-specific cytotoxic T lymphocyte responses induced with genetically modified DCs that express CEA. International Journal of Oncology, vol. 32 (2008) pp. 459-466.*
A. Hovden, et al., "Maturation of monocyte derived dendritic cells with OK432 boosts IL-12p70 secretion and conveys strong T-cell responses", BMC Immunology 12:2 (2011).
English translation of International Search Report for corresopnding PCT/KR2013/004750.
M. Sato et al., "Generation of mature dendritic cells fully capable of T helper type 1 polarization using OK-432 combined with prostaglandin E2," Cancer Science, vol. 94, No. 12, pp. 1091-1098 (Dec. 2003).
S. Nakahara et al., "Dendritic Cells Stimulated with a Bacterial Product, OK-432, Efficiently Induce Cytotoxic T Lymphocytes Specific to Tumor Rejection Peptide," Cancer Research, American Association for Cancer Research, US, vol. 63, No. 14, pp. 4112-4118 (Jul. 2003).

* cited by examiner

*Primary Examiner* — Kara Johnson
(74) *Attorney, Agent, or Firm* — Fitzpatrick, Cella, Harper & Scinto

(57) ABSTRACT

The present invention relates to a composition for maturing dendritic cells, comprising, as a maturation-promoting factor, Interleukin-1β (IL-1β), Interleukin-6 (IL-6), Tumor necrosis factor-α (TNF-α), Interferon-γ (IFN-γ), Prostaglandin E2 (PGE2), Picibanil (OK432) and/or Poly IC. The composition for maturing dendritic cells of the present invention may have the effects of not only improving the ability of dendritic cells to induce an immune response, but also of decreasing the antigen non-specific immune response of dendritic cells and increasing antigen-specific immune response of dendritic cells, thus maximizing the effects of immunotherapy.

4 Claims, 17 Drawing Sheets

COMPOSITION FOR MATURING DENDRITIC CELLS, AND METHOD FOR PREPARING ANTIGEN-SPECIFIC DENDRITIC CELLS USING SAME

BACKGROUND OF THE INVENTION

1. Technical Field

The present invention relates to a composition for maturing dendritic cells, and a method for preparing antigen-specific dendritic cells using the same.

2. Description of the Related Art

Dendritic cells (DCs) are antigen-presenting cells (APCs) that have the most potent ability to present antigens among cells of the immune system. A dendritic cell stimulates a T cell that has not been exposed to antigen (termed naïve T cell), inducing an immune reaction. Hence, a dendritic cell is a unique immune cell that, unlike other APCs, can both effectively induce a primary immune response and activate memory T cells. A dendritic cell is known to express co-stimulatory molecules at a high concentration as well as MHC molecules (I/II) on the surface thereof, and to release cytokines (IFN-alpha, IL-12, IL-18) necessary for T cell activation. This is why dendritic cells can induce a potent immune response. Releasing Th1 immunity related cytokines such as IFN-alpha, IL-12, etc., type 1 dendritic cells can induce the proliferation of antigen-specific Th1 cells and the activation of cytotoxic T lymphocytes (CTL), and thus have useful applications in immunotherapy.

For utilizing dendritic cells in the immunotherapy of cancer, a technique for in vitro differentiating monocytes into dendritic cells and maturing the immature dendritic cells to mature ones useful in inducing T cell immunity is indispensable. Neither techniques of preparing immature dendritic cells from monocytes in vivo nor a maturation process have yet been standardized in the art. Particularly, the maturation of the immature dendritic cells differentiated from monocytes is achieved through a process in which the immature dendritic cells are allowed to migrate to lymph nodes where they present an antigen fragment to naïve T cells to induce a Th1 immune response. Fully mature dendritic cells express MHC I and II molecules and T cell co-stimulatory molecules, i.e., CD80 and CD86, at a high concentration on their surface, compared to immature dendritic cells. In addition, mature dendritic cells secrete many of cytokines that are directly involved in the induction of T cell immune responses. After undergoing this change by maturation, the dendritic cells greatly increase in the potential of inducing T cell immune responses.

MCM (monocyte conditioned medium) is known as being useful for the maturation of dendritic cells. MCM, which produced by culturing monocytes in vitro, is used as a source of maturation factors. MCM approach, however, does not guarantee an uniform condition from one maturation process to another because proinflammatory cytokines that monocytes release in response to external signals greatly vary in quantity from person to person. In addition, an additional disadvantage is the requirement of a large quantity of peripheral blood monocytes for preparing MCM. As an alternative to the MCM approach, a cytokine cocktail of important cytokines (IL-1β, IL-6, TNF-α, PGE$_2$) selected from among MCM components was developed. The cytokine cocktail can allow for the stable production of dendritic cells with relatively high function, as well as solving the problems of MCM. However, the cytokine cocktail alone cannot render sufficiently mature dendritic cells.

Korean Patent Application Unexamined Publication No. 10-2011-0035633 discloses the in vitro generation of cytotoxic T cells by using Th1 cells and dendritic cells. However, since this method utilizes dendritic cells that are not yet matured fully, it is difficult to expect substantially sufficient immunotherapy therefrom.

There is therefore a strong need for a more effective maturation technique of dendritic cells by which potent antigen-specific immunity against cancer can be induced, leading to a maximum immunotherapeutic effect on cancer.

SUMMARY OF THE INVENTION

It is therefore an object of the present invention to provide a composition for maturating dendritic cells that potentiates the ability of dendritic cells to induce an immune response, decreases antigen non-specific immune responses of dendritic cells, and increases antigen-specific immune responses of dendritic cells, thereby exerting a maximum immunotherapeutic effect.

It is another object of the present invention to provide antigen-specific dendritic cells prepared by using the composition for maturing dendritic cells.

It is a further object of the present invention to provide a method for preparing antigen-specific dendritic cells.

In accordance with an aspect thereof, the present invention provides a composition for maturating dendritic cells, comprising, as a maturation factor, at least one selected from among Interleukin-1β (IL-1β), Interleukin-6 (IL-6), Tumor necrosis factor-α (TNF-α), Interferon gamma (IFN-γ), Prostaglandin E2 (PGE2), Picibanil (OK432) and Poly IC.

In accordance with another aspect thereof, the present invention provides an antigen-specific dendritic cell, prepared by using the composition.

In accordance with a further aspect thereof, the present invention provides a method for preparing antigen-specific dendritic cells, comprising: pulsing immature dendritic cells with an antigen; and treating the pulsed dendritic cells with at least one maturation factor selected from among Interleukin-1β (IL-1β), Interleukin-6 (IL-6), Tumor necrosis factor-α (TNF-α), Interferon gamma (IFN-γ), Prostaglandin E2 (PGE2), Picibanil (OK432) and Poly IC.

In addition to enhancing the ability of dendritic cells to induce an immune response, the composition of the maturation composition of the present invention can increase antigen-specific T cell immune responses, with the concomitant decrease of non-specific immune responses, thereby bringing about a maximal immunotherapeutic effect.

DESCRIPTION OF THE PREFERRED EMBODIMENTS

Figure 1:
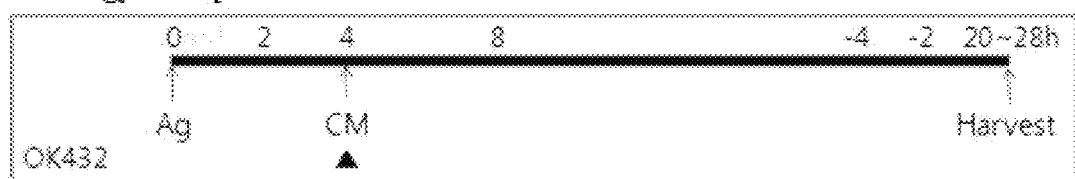
FIG. 1 is a schematic scheme of the preparation of mature dendritic cells by treating with an antigen (Ag) and all maturation factors (CM) simultaneously (B), or at a time lag only for Picibanil (OK432) of the maturation factors (A).
Figure 1:
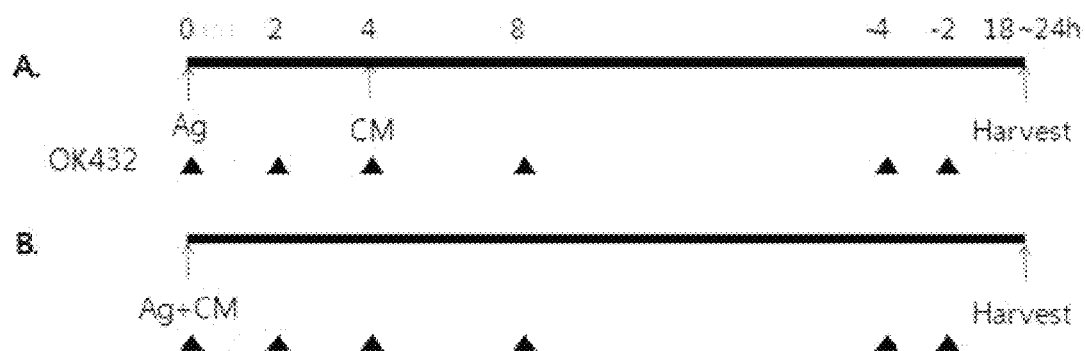

In accordance with an aspect thereof, the present invention addresses a composition for maturating dendritic cells, comprising a maturation factor including Picibanil (OK432). In particular, the present invention is completed by the inventor through finding that the dendritic cells matured by treatment with Picibanil (OK432) of the maturation factors and an antigen with a time interval therebetween have remarkably improved ability to induce an immune response. Further, by the dendritic cells of the present application, antigen-nonspecific immune response is decreased and antigen-specific immune response is increased so that the immunotherapeutic effect gets maximized.

The maturation factor useful in the present invention may be at least one selected from among Interleukin-1β(IL-1β), Interleukin-6 (IL-6), Tumor necrosis factor-α (TNF-α), IFN-γ, Prostaglandin E2 (PGE2), Picibanil (OK432) and Poly IC, with preference for Picibanil (OK432).

The Picibanil (OK432) is an anti-tumor medication designed to augment cellular immunity and is made of a lyophilized haemolytic *streptococcus* pretreated with penicillin. So long as it is referred to as Picibanil (OK432) in the art, any agent may be used in the present invention without specific limitations. Although originally developed for the therapy of digestive system cancer, thyroid cancer, and lung cancer, Picibanil (OK432) is used as a dendritic cell-maturing factor to greatly potentiate the ability of dendritic cells to induce an immune response in the present invention. Also, any substance selected from among Interleukin-1β (IL-1β), Interleukin-6 (IL-6), Tumor necrosis factor-α (TNF-α), Interferon gamma (IFN-γ), Prostaglandin E2 (PGE2) and Poly IC may be used in the present invention without limitation.

The dendritic cells of the present invention exhibit an excellent immune response-inducing potential, without dependence on media, such as RPMI (Roswell Park Memorial Institute) 1640, serum-free X-VIVO 15, etc.

The maturation composition according to the present invention can not only enhance the ability of dendritic cells to induce an immune response, but also can increase an antigen-specific immune response with a concomitant reduction in nonspecific immune responses.

In accordance with another aspect thereof, the present invention addresses a dendritic cell, prepared by using the maturation composition, capable of inducing an antigen-specific immune response.

In accordance with a further aspect thereof, the present invention addresses a method for preparing a dendritic cell capable of inducing an antigen-specific immune response, comprising pulsing an immature dendritic cell with an antigen; and treating the pulsed dendritic cell with a maturation factor.

The pulsing with an antigen and the treatment with a maturation factor may be conducted simultaneously or sequentially. For example, the cell may be incubated with an antigen and a maturation factor simultaneously. Alternatively, 1 to 30 hours after pulsing with an antigen, the cell may be treated with a maturation factor. This is the preferred method.

Particularly when Picibanil and a different maturation factor are employed, they are more preferably applied with a time interval therebetween. That is, the cell may be treated with at least one selected from among Interleukin-1β (IL-1β), Interleukin-6 (IL-6), Tumor necrosis factor-α (TNF-α), Interferon gamma (IFN-γ), Prostaglandin E2 (PGE2), and Poly IC, followed by incubation with Picibanil (OK432). Preferably, treatment with a combination of the maturation factors other than Picibanil is conducted simultaneously or within 1 hour after pulsing with an antigen. As for Picibanil, its application is preferably conducted 1 hour after pulsing an antigen, and more preferably after pulsing with an antigen and treatment with other maturation factors and 1 to 4 hours before the harvest of dendritic cells.

Treatment with Picibanil at a predetermined time after treatment with a maturation factor other than Picibanil allows the dendritic cells to decrease in nonspecific immune response and to exhibit a maximum antigen-specific immune response.

The maturation factors are as defined above.

Dendritic cells are antigen presenting cells which have the most potent ability to present antigens among the cells of the immune system. Thus, the dendritic cells have ability to present to MHC I/II molecules through antigen uptake and antigen processing, in which a type of the antigen is not specially limited to large recombinant proteins or peptides, cancer lysates, ribonucleic acids, fusions to cancer cells, or apoptotic or necrotic cancer cells. Hence, the dendritic cells can avail antigens without limitations to specific types. Examples of the antigens available in the present invention include, but are not limited to, AFP (alpha-fetoprotein), GPC-3 (Glypican-3), PSA (prostate specific antigen), MAGE-1 (Melanoma-Associated Antigen 1), PSMA (prostate-specific membrane antigen), PAP (prostatic acid phosphatase), and a lysate of cancer cell line, or a cancer tissue.

A better understanding of the present invention may be obtained through the following examples which are set forth to illustrate, but are not to be construed as limiting the present invention.

EXAMPLES AND COMPARATIVE EXAMPLES

Mature dendritic cells of Examples and Comparative Examples were prepared, as shown in Table 1, below.

supplemented with the plasma taken from the same person, and was cultured in an incubator. When frozen PBMC was used, PBMC was thawed and washed with HBSS and a serum-free medium before use.

For segregation of monocytes from PBMC, the characteristic of monocytes to adhere to the plastic bottom of cell culture dishes or plates was available. In detail, after PBMC suspended in a medium was incubated at 37° C., non-adherent cells were discarded together with the medium, and thus adherent cells, in which monocytes were selectively adjusted to 80% or higher of the total blood cells, were obtained.

RPMI 1640 supplemented with a cytokine cocktail (human recombinant protein IL-4 (Interleukin-4, final concentration: 500 ng/mL or less) expressed in $E.\ coli$) and GM-CSF (JW CreaGene, final concentration: 100 ng/mL or less) was used as a medium for inducing differentiation from monocytes to dendritic cells.

(2) Pulsing Immature Dendritic Cell with Antigen

After three days of incubation, floating cells that were detached from the bottom were harvested, counted, and incubated at a predetermined density in the presence of an antigen.

For a cancer-specific immune response, the cells were treated with a predetermined concentration of a tumor-specific or associated antigen (AFP, GPC-3 or MAGE-1; 5~10 μg/mL, JW CreaGene), or a cancer lysate (T98G tumor cell line lysate; 50-100 μg/mL, in-house).

(3) Maturation of Immature Dendritic Cell (imDC→mDC)

Immature dendritic cells were matured simultaneously with the antigen pulsing (2) (FIG. 1B). For maturation, the

TABLE 1

|  | Ex. 1 (MAGE-1, AFP, GPC-3/OK+) | Ex. 2 | C. Ex. 1 (MAGE-1, AFP, GPC-3/OK−) | C. Ex. 2 (Un/OK+) | C. Ex. 3 (MAGE-1, AFP, GPC-3/OK−) | C. Ex. 4 (Un/OK−) |
| --- | --- | --- | --- | --- | --- | --- |
| Antigen | MAGE-1 (Ex. 1-1) AFP (Ex. 1-2), GPC-3 (Ex. 1-3) | MAGE-1 (Ex. 2-1) AFP (Ex. 2-2), GPC-3 (Ex. 2-3) | MAGE-1 (C. Ex. 1-1) AFP (C. Ex. 1-2), GPC-3 (C. Ex. 1-3) | Untreated | MAGE-1 (C. Ex. 3-1) AFP (C. Ex. 3-2), GPC-3 (C. Ex. 3-3) | Untreated |
| Maturation Factor | Other than OK432 Treatment with Picibanil/ Time | IL-1β, IL-6, TNF-α, IFN-γ, PGE$_2$, Poly IC Treated/ Simultaneously | IL-1β, IL-6, TNF-α, IFN-γ, PGE$_2$, Poly IC Treated/ Time lag | IL-1β, IL-6, TNF-α, PGE$_2$ Untreated/— | IL-1β, IL-6, TNF-α, IFN-γ, PGE$_2$, Poly IC Treated/ Simultaneously | IL-1β, IL-6, TNF-α, IFN-γ, PGE$_2$, Poly IC Untreated/— | IL-1β, IL-6, TNF-α, IFN-γ, PGE$_2$, Poly IC Untreated/— |

Example 1

Preparation of Dendritic Cells by Simultaneous Treatment with an Antigen and Maturation Factor Mature dendritic cells of Example 1 were prepared as described in Table 1.

(1) Differentiation from Peripheral Blood Mononuclear Cell (PBMC) to Immature Dendritic Cell (PBMC→imDC)

A blood sample taken from a healthy person was subjected to density gradient centrifugation at temperature using Ficoll-Paque Plus (Endotoxin-free grade) to separate peripheral blood mononuclear cells (PBMC) in which reticulocytes, granulocytes, platelets, and plasma were removed.

After being harvested by centrifugation, the PBMC was suspended at a predetermined concentration in RPMI 1640 immature dendritic cells were incubated with TNF-α (Tumor necrosis factor-α; 10 ng/mL), IL-1β (Interleukin-1β; 10 ng/mL), IL-6 (Interleukin-6; 10 ng/mL), and PGE2 (Prostaglandin E2; 1 μg/mL). To this medium, Poly IC (final concentration 10 μg/mL), Picibanil (medication, OK432, JW Pharmaceutical, final concentration 1-2 μg/mL), and IFN-γ (LG Life Science, final concentration 30~1000 U/mL) were also added to stimulate immature dendritic cells through toll like receptors.

On the final day of incubation, floating cells were harvested, washed twice, and suspended in a cryopreserving medium (DMSO-containing human serum albumin or human plasma) to give a stock.

Example 2

Preparation of Dendritic Cell by Treatment with Picibanil (OK432) at Time Lag

Dendritic cells were prepared in the same manner as in Example 1, with the exception that Picibanil was applied 4 hrs after treatment with the antigen (2) and the maturation factors other than Picibanil (3) (FIG. 1A).

Example 3

Preparation of Dendritic Cell by Treatment with Picibanil (OK432) at Time Lag

Dendritic cells were prepared in the same manner as in Example 1, with the exception that time points at which the antigen (2), a maturation factor other than Picibanil (3), and Picibanil (OK432) were applied were controlled as follows (FIG. 1).

TABLE 2

| | Treatment with Picibanil (OK432) |
|---|---|
| Ex. 3-1 | Simultaneous treatment with antigen (2) and Picibanil-containing composition (3) |
| Ex. 3-2 | Treatment with antigen (2) and maturation factor other than Picibanil (3), followed by treatment with Picibanil, 2 hrs later |
| Ex. 3-3 | Treatment with antigen (2) and maturation factor other than Picibanil (3), followed by treatment with Picibanil, 4 hrs later |
| Ex. 3-4 | Treatment with antigen (2) and maturation factor other than Picibanil (3), followed by treatment with Picibanil 4 hrs before harvest of dendritic cells |
| Ex. 3-5 | Treatment with antigen (2) and maturation factor other than Picibanil (3), followed by treatment with Picibanil 2 hrs before harvest of dendritic cells |

Comparative Examples 1 to 4

Preparation of Dendritic Cell without Pulsing with Antigen or Treatment with Picibanil (OK432)

According to the constitutions stated the above Table 1, dendritic cells were prepared in the same manner as in Example 1, with the exception that the cells were not treated with the antigen (2) and/or with Picibanil.

EXPERIMENTAL EXAMPLES

Experimental Example 1

Assay for Cytokines Released from Dendritic Cells During Maturation

Figure 2:
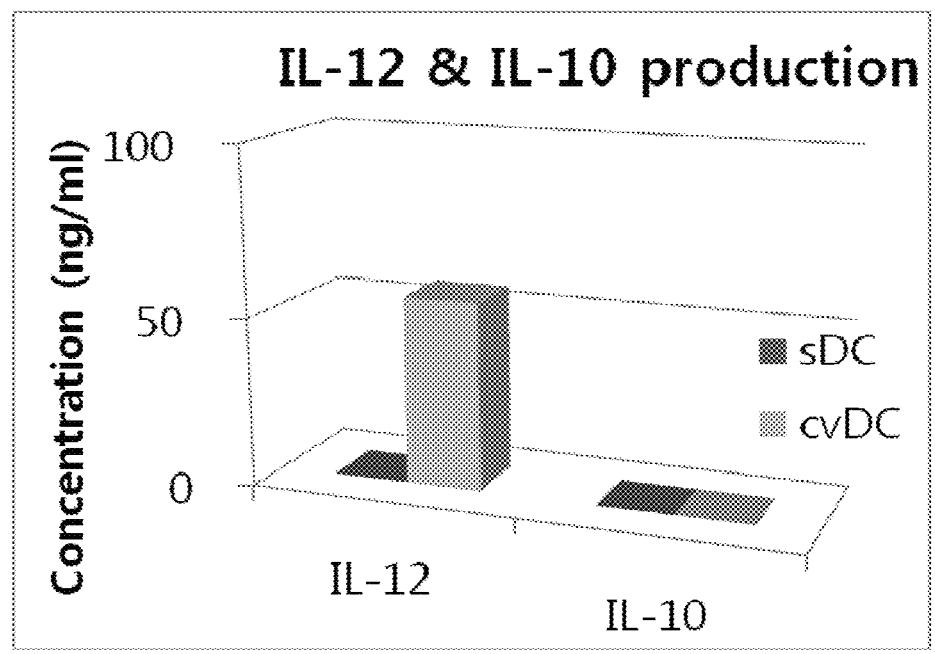
FIG. 2 is a graph showing levels of IL-12 and IL-10 released in the culture of the dendritic cells during the maturation of dendritic cells in Example 1-1 (MAGE-1/OK+) and Comparative Example 1-1 (MAGE-1/OK−). In the graph, cvDC and sDC represent dendritic cells prepared in Example 1-1 and Comparative Example 1-1, respectively.
Figure 3:
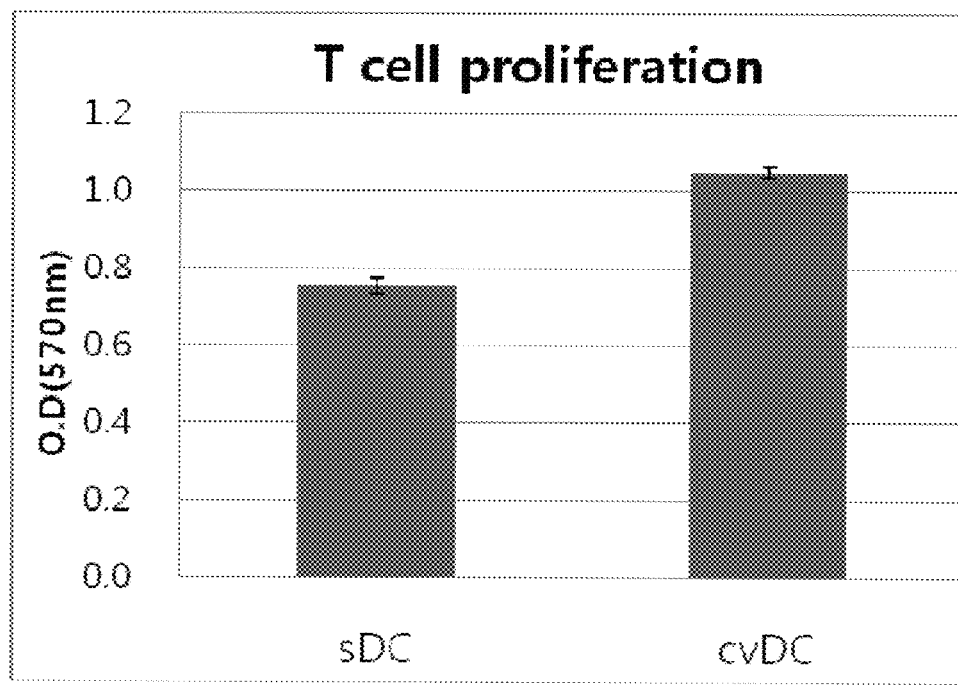
FIG. 3 is a graph showing T cell proliferation when T cells isolated from peripheral blood cells were co-cultured with the dendritic cells of Example 1-1 (MAGE-1) or Comparative Example 1-1, as measured by MTT assay. In the graph, cvDC and sDC represent dendritic cells prepared in Example 1-1 and Comparative Example 1-1, respectively.
Figure 4:
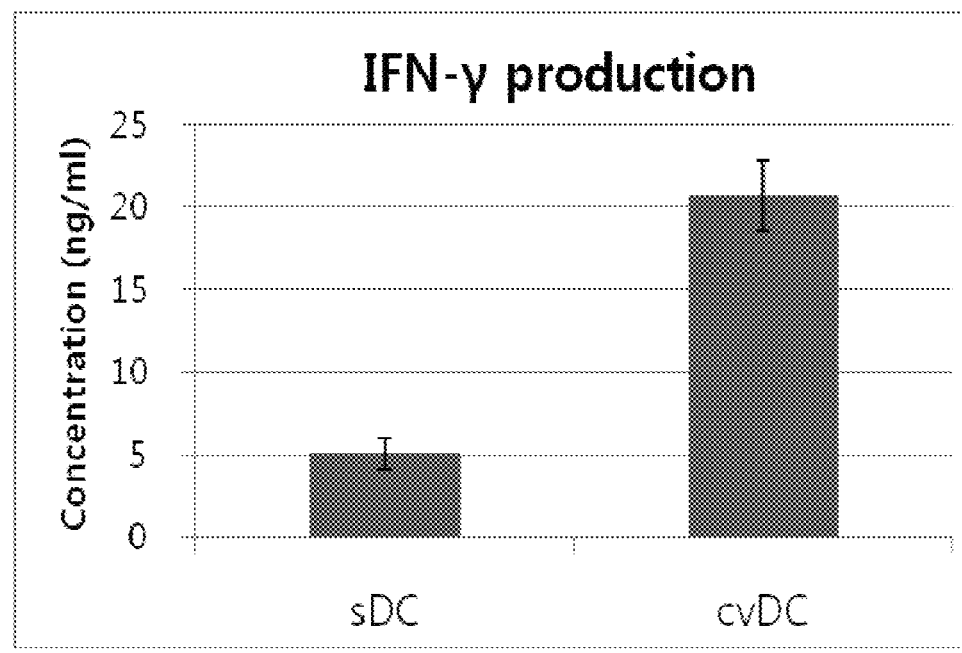
FIG. 4 is a graph showing levels of IFN-γ in culture supernatant when T cells isolated from peripheral blood cells were co-cultured with the dendritic cells of Example 1-1 (MAGE-1) or Comparative Example 1-1, as measured by ELISA. In the graph, cvDC and sDC represent dendritic cells prepared in Example 1-1 and Comparative Example 1-1, respectively.

During the maturation of dendritic cells in Example 1-1 (MAGE-1/OK+) and Comparative Example 1-1 (MAGE-1/OK−), IL-12 and IL-10 released in the culture of the dendritic cells were measured, and the results are depicted in FIG. 2. When T cells isolated from peripheral blood were co-cultured with the dendritic cells of Example 1-1 or Comparative Example 1-1, evaluation was made of T cell proliferation and IFN-γ level, and the results are shown in FIGS. 3 and 4, respectively.

In detail, levels of IL-12 and IL-10 in the culture of dendritic cells during antigen treatment and maturation were determined using ELISA according to the instruction provided by the manufacturer. The results are shown in FIG. 2.

Separately, T cell proliferation was evaluated. Autologous T cells purified using nylon wool were seeded at a density of $1\times10^5$ cells/well at a ratio of 10:1 with $1\times10^4$ dendritic cells, and cultured in triplicate for 5 days in 96-well plates. Thereafter, MTT assay was performed to measure live T cells. The result is given in FIG. 3.

After autologous T cells and dendritic cells were co-cultured for 5 days, the level of IFN-γ in the culture was measured using ELISA. The result is depicted in FIG. 4.

Experimental Example 2

Non-Specific T Cell Induction by Picibanil (OK432)

To evaluate the effect of Picibanil (OK432) on non-specific T cell induction, experiments were performed on mature dendritic cells (mDC) prepared in the Examples and Comparative Examples, as follows.

Figure 5:
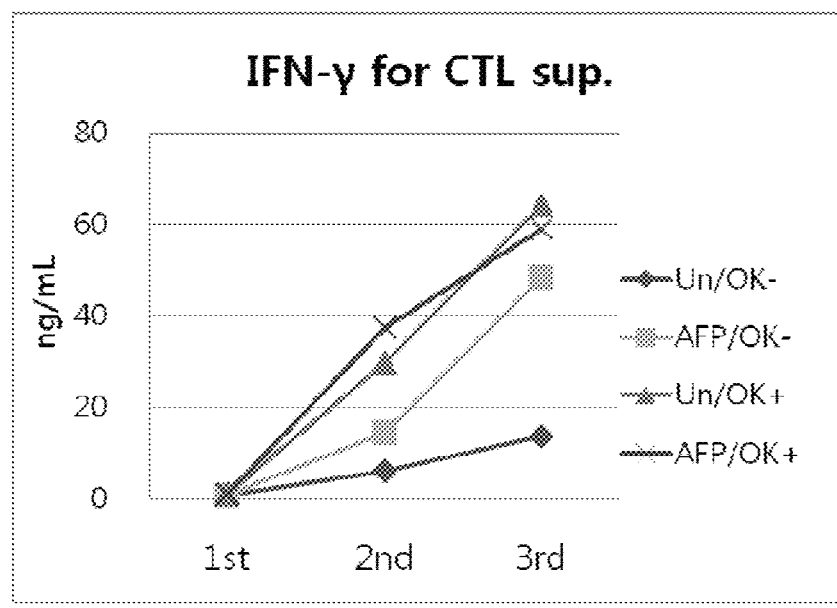
FIG. 5 is a graph showing levels of IFN-γ released to the media over three rounds of measurement during each of which autologous T cells were stimulated with dendritic cells of Example 1-2 (AFP/OK+), Comparative Example 2 (Un/OK+), Comparative Example 3-2 (AFP/OK−) and Comparative Example 4 (Un/OK−), with a predetermined mixture ratio set between the cells.

Autologous T cells isolated from peripheral blood mononuclear cells (PBMC) were incubated with dendritic cells of Example 1-2 (AFP/OK+), Comparative Example 2 (Un/OK+), Comparative Example 3-2 (AFP/OK−) and Comparative Example 4 (Un/OK−), as follows. On day 1 of each stimulation, levels of IFN-γ in the cultures were measured. In this regard, T cells were purified from the peripheral blood taken from the same person used for the preparation of dendritic cells, using nylon wool. The mature dendritic cells and the purified T cells were mixed at a ratio of 1:10 ($2\times10^5$ : $2\times10^6$) for 6~7 days. After primary stimulation, the T cells were harvested, and stimulated again by the antigen-pulsed dendritic cells, with the same ratio (1:10) set therebetween. The medium (RPMI 1640+10% AB serum) was replaced by a fresh medium every 2~3 days to maintain a proper culture condition. On primary stimulation, IL-7 (Peprotech) was added at a concentration of 5 ng/mL. Since secondary stimulation, cells were treated with 100 U/mL IL-2 (Proleukin). T cells were stimulated 2~4 times with the antigen-pulsed DCs to induce CTL that was then assayed for antigen specificity and activity. On the day after stimulation on the T cells co-cultured with the dendritic cells, a supernatant sample was taken, and quantitatively analyzed for IFN-γ using ELISA. The result is given in FIG. 5.

Figure 6:
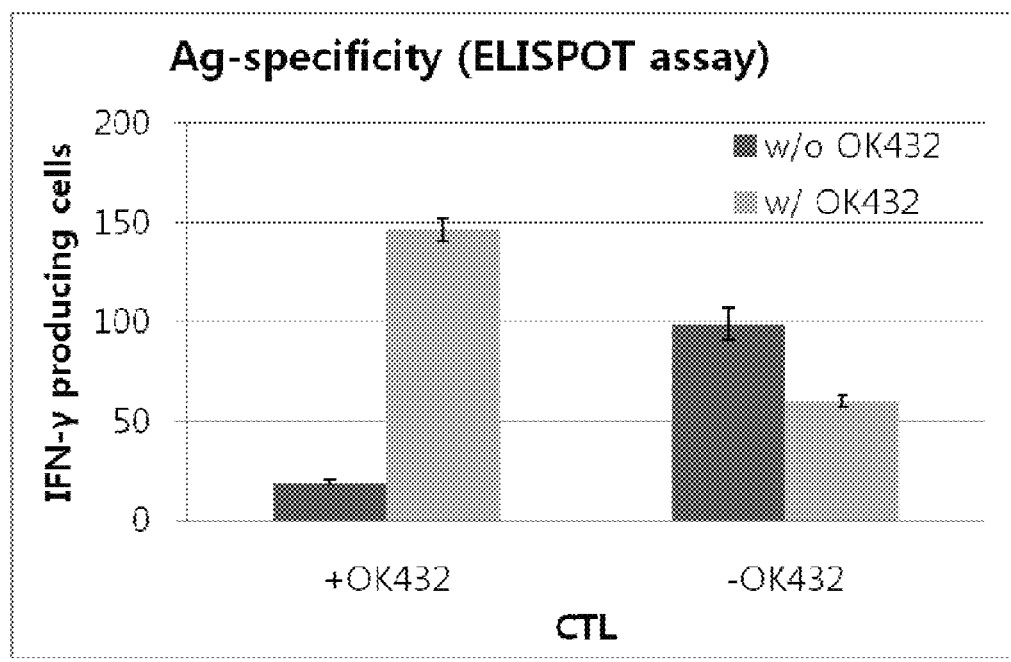
FIG. 6 is a graph demonstrating the antigen-specificity of CTL induced by dendritic cells of Example 1-3 (GPC-3/OK+) and Comparative Example 2 (Un/OK+), Comparative Example 3-3 (GPC-3/OK−), and Comparative Example 4 (Un/OK−), as measured by IFN-γ ELISPOT analysis.

In addition, T cells that were activated by the dendritic cells stimulated with the GPC-3 antigen were assayed for antigen-specific immune response. For this, CTL induced with dendritic cells of Example 1-3 (GPC-3/OK+), Comparative Example 2 (Un/OK+), Comparative Example 3-3 (GPC-3/OK−), and Comparative Example 4 (Un/OK−) were assessed for antigen specificity using IFN-γ ELISPOT assay. In detail, after co-cultured with dendritic cells in the presence or absence of Picibanil (OK432) (FIG. 6), IFN-γ producing cells were counted. Activated T cells ($1\sim2\times10^4$ cells) and dendritic cells ($1\sim2\times10^3$ cells) were co-cultured at a ratio of 10:1 for 18-24 hrs in an incubator, followed by ELISPOT analysis according to the instruction included in the kit. The result is shown in FIG. 6.

Also, CTL activity and antigen-specific T cell response of the induced CTL were performed. For this, the CTL stimulated by dendritic cells of Example 1-2 (AFP/OK+), Comparative Example 2 (Un/OK+), Comparative Example 3-2 (AFP/OK−) and Comparative Example 4 (Un/OK−) were reacted with target cells, and a level of the IFN-γ secreted to the medium was measured. In detail, HepG2 cells ($1\times10^4$ cells) that were found to match in HLA type with CTL and to express an antigen (AFP) were co-cultured with CTL ($1\times10^5$ cells) at a ratio of 1:10 for 18~24 hrs in an incubator, and then the supernatant was taken and quantitatively analyzed for IFN-γ using ELISA. Measurements of the IFN-γ levels are depicted in Table 7.

Figure 7:
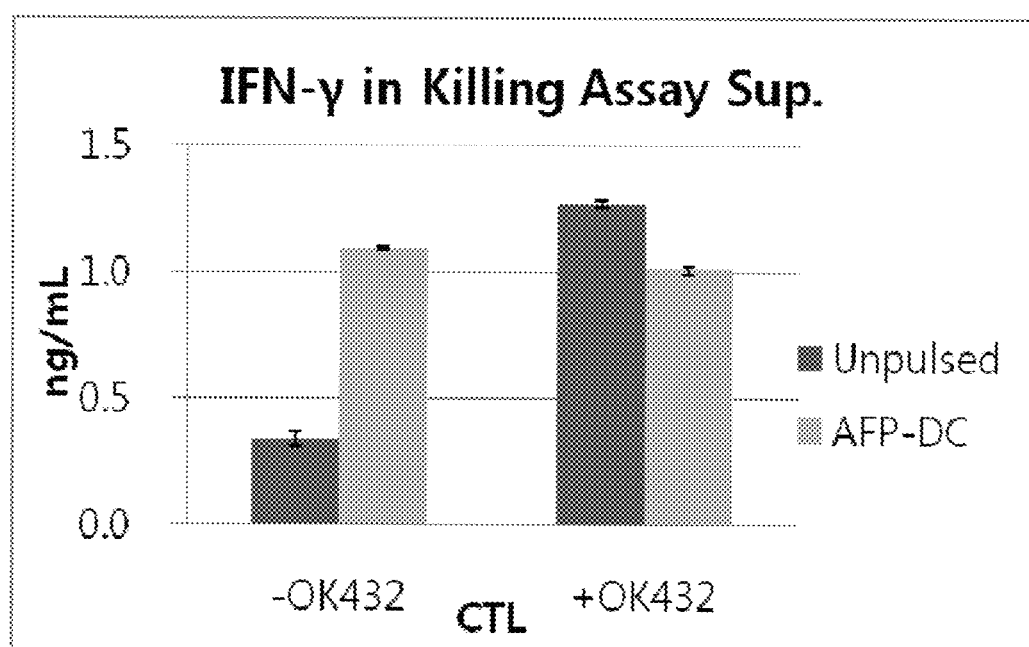
FIG. 7 is a graph showing levels of IFN-γ released to the media when CTL activated by dendritic cells of Example 1-2 (AFP/OK+), Comparative Example 2 (Un/OK+), Comparative Example 3-2 (AFP/OK−) and Comparative Example 4 (Un/OK−) reacted with target cells.

From the data of FIG. 7, it is understood that treatment of dendritic cells with Picibanil (OK432) results in potent antigen-nonspecific T cell induction.

Experimental Example 3

Effect of Picibanil (OK432) on Maturation of Dendritic Cell

Dendritic cells (DC) that were treated with Picibanil (OK432) during maturation after antigen pulsing were functionally compared to those that were not treated. In this regard, CTL was induced using AFP- or GPC-3-stimulated dendritic cells of Example 1-2 (AFP/OK+), Comparative Example 3-2 (AFP/OK−), Example 1-3 (GPC-3/OK+), and Comparative Example 3-3 (GPC-3/OK−), and was analyzed for proliferation and maturation effect.

Figure 8:
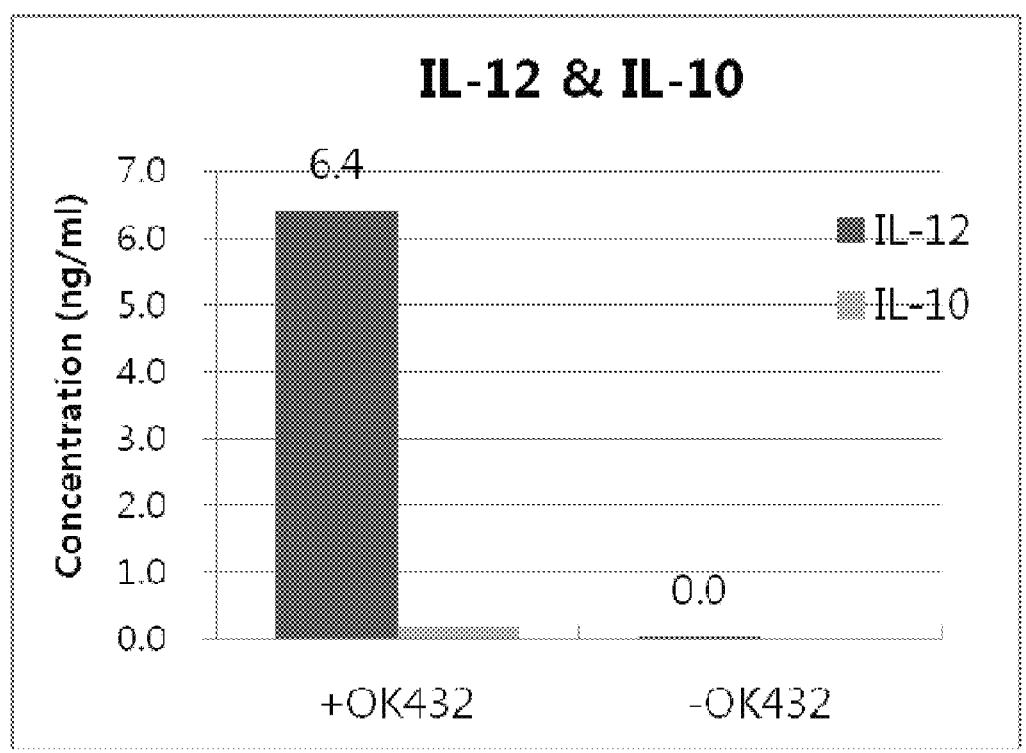
FIG. 8 is a graph showing levels of IL-12 and IL-10 that dendritic cells of Example 1-2 (AFP/OK+) and Comparative Example 3-2 (AFP/OK−) released to the media during their maturation.

In detail, when dendritic cells of Example 1-2 (AFP/OK+) and Comparative Example 3-2 (AFP/OK−) were prepared, levels of IL-12 and IL-10 in the media during the maturation were measured using ELISA, and the results are shown in FIG. 8.

Figure 9:
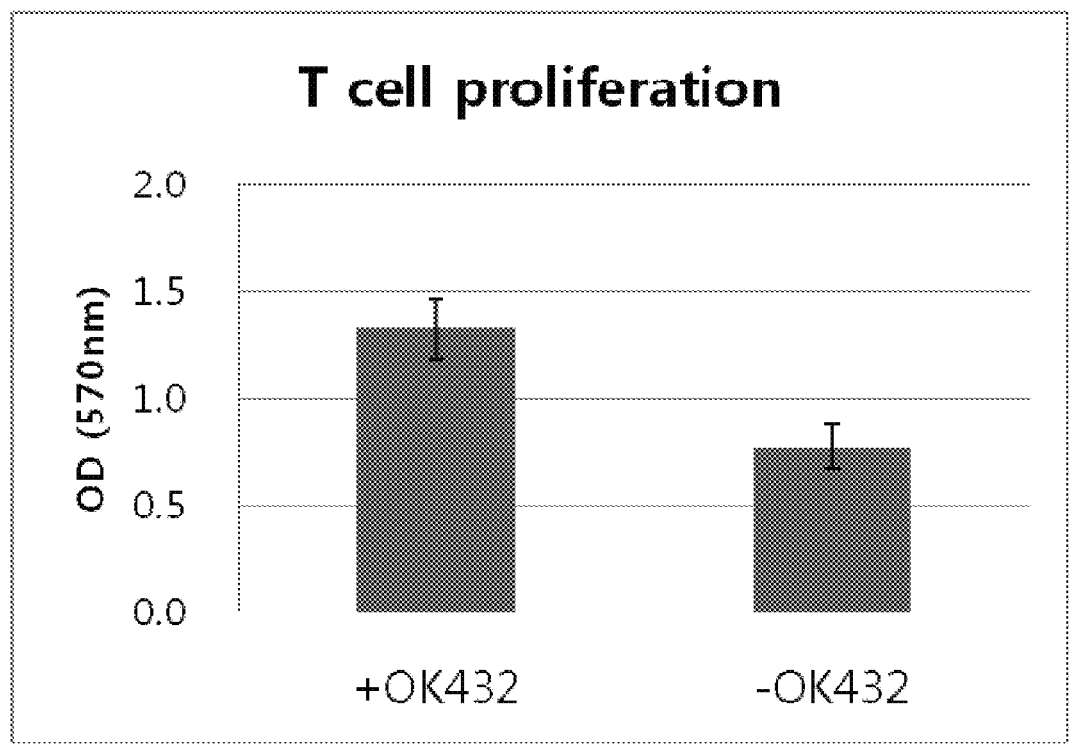
FIG. 9 is a graph showing T cell proliferation when T cells purified from peripheral blood cells were co-cultured with dendritic cells of Example 1-3 (GPC-3/OK+) and Comparative Example 3-3 (GPC-3/OK−), as measured by MTT assay.

T cells ($1\times10^5$ cells) purified using nylon wool and dendritic cells ($1\times10^4$ cells) of Example 1-3 (GPC-3/OK+) and Comparative Example 3-3 (GPC-3/OK−) were co-cultured at a ratio of 10:1 for 5 days in triplicate in 96-well plates. Thereafter, cell proliferation was examined by counting viable cells after staining with MTT, and the results are given in FIG. 9.

Figure 10:
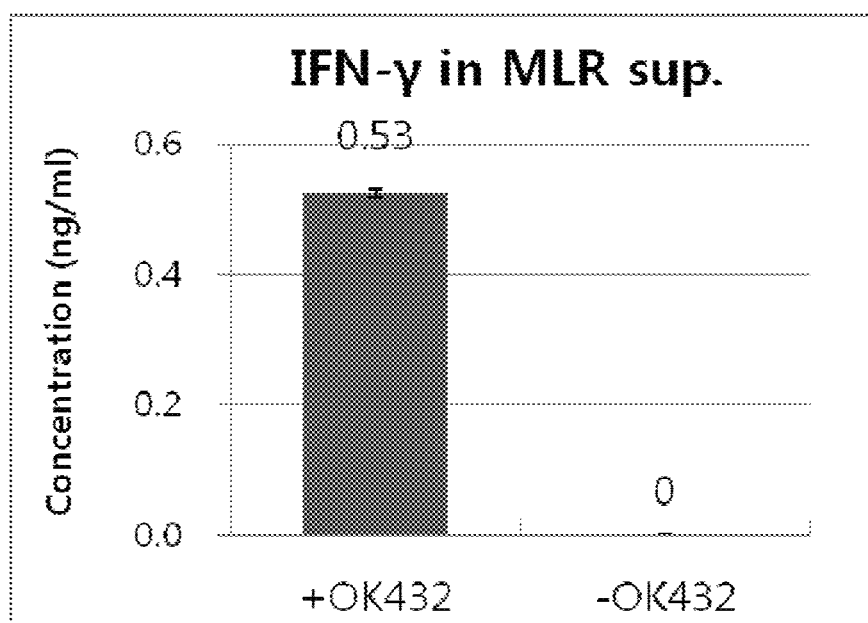
FIG. 10 is a graph showing levels of IFN-γ in culture media when T cells purified from peripheral blood cells were co-cultured with dendritic cells of Example 1-2 (AFP/OK+) and Comparative Example 3-2 (AFP/OK−), as measured by ELISA.

In addition, when T cells isolated from peripheral blood cells were co-cultured with the dendritic cells of Example 1-2 (AFP/OK+) and Comparative Example 3-2 (AFP/OK−), levels of IFN-γ in the media were analyzed using ELISA, and the results are shown in FIG. 10.

Figure 11:
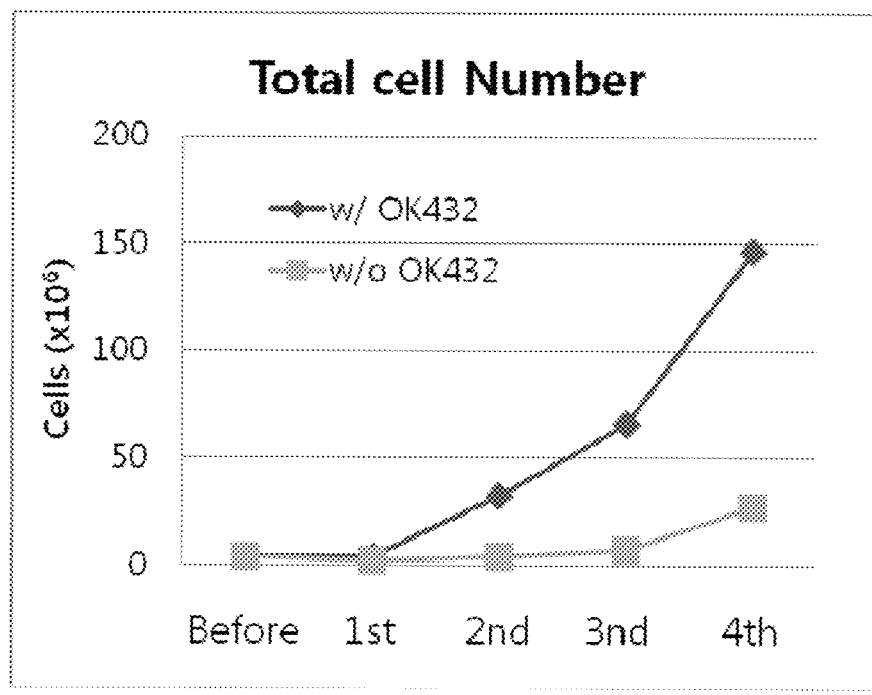
FIG. 11 is a graph showing cell proliferation in each stage of the amplification of CTL by dendritic cells of Example 1-3 (GPC-3/OK+) and Comparative Example 3-3 (GPC-3/OK−).
Figure 12:
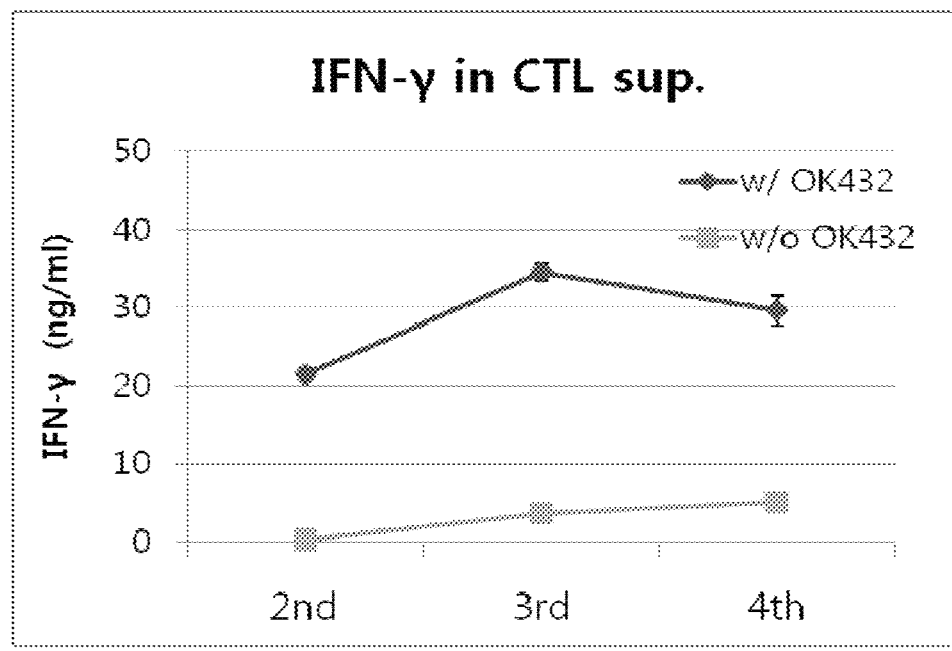
FIG. 12 is a graph showing levels of IFN-γ in the media upon CTL induction with dendritic cells of Example 1-3 (GPC-3/OK+) and Comparative Example 3-3 (GPC-3/OK−), as measured by ELISA.

Further, cell proliferation was measured after each CTL stimulation with dendritic cells of Example 1-3 (GPC-3/OK+) and Comparative Example 3-3 (GPC-3/OK−), and the result is depicted in FIG. 11. On day 1 of each stimulation of T cells with the dendritic cells, the supernatants were taken and analyzed for ELISA IFN-γ level using ELISA, and the result is depicted in FIG. 12.

As shown in the figures, treatment with Picibanil (OK432) increased a level of IL-12, which is important for Th1 immune response induction (FIG. 8: antigen AFP), induced T cell proliferation (FIG. 9: antigen GPC-3), and potentiated Th1 immune responses (FIG. 10: antigen AFP). Also, the treatment with Picibanil was found to bring about an improvement in the proliferation (FIG. 11, antigen GPC-3) and function (IFN-γ) (FIG. 12: antigen GPC-3) of activated T cells.

Experimental Example 4

Effect of Treatment with Antigen and Picibanil (OK432) at Time Lag (RPMI 1640)

Dendritic cells of Examples 1-3 and 2-3 in which maturation was induced with Picibanil (OK432) at different times after pulsing with the antigen GPC-3 were subjected to ELISPOT assay and cytotoxicity test (CV).

Figure 13:
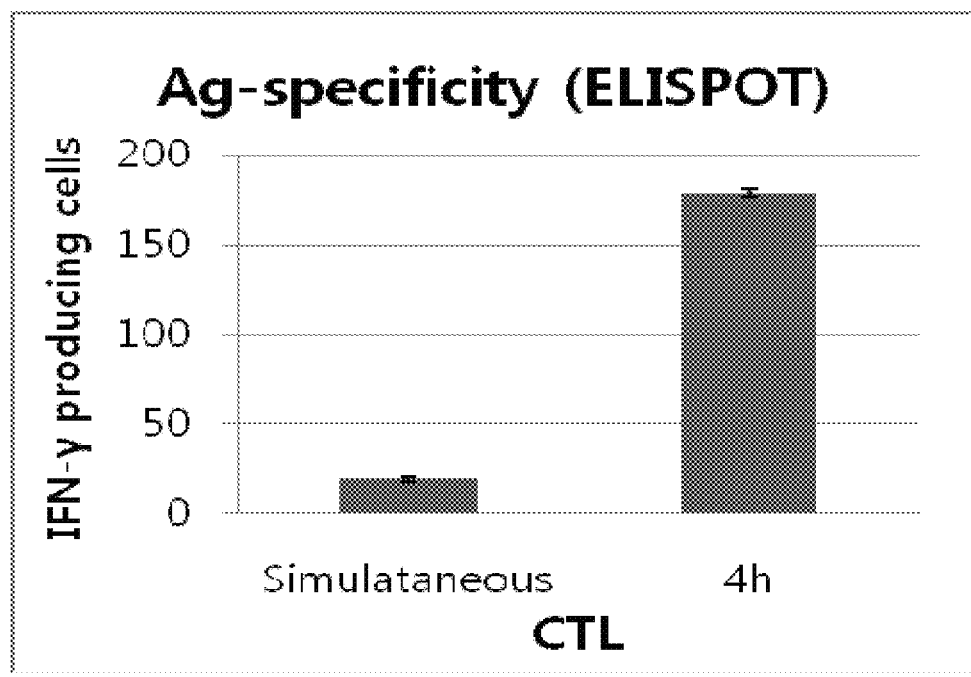
FIG. 13 is a graph showing antigen specificity of the CTL activated by dendritic cells of Example 1-3 (GPC-3/OK+) and Example 2-3 (GPC-3/OK+), as measured by IFN-γ ELISPOT analysis. As in FIG. 1B, the CTL was induced by dendritic cells that were treated with Picibanil (OK432) 0 or 4 hrs after treatment with an antigen and a maturation factor other than Picibanil.

Dendritic cells were treated with Picibanil (OK432) simultaneously with the antigen and the maturation factors (Example 1-3, simultaneous) or 4 hours after treatment with the antigen and the maturation factors (Example 2-3, 4 h). CTL ($15\times10^4$ cells) induced by treating autologous T cells with the dendritic cells was co-cultured for 18~20 hrs at a ratio of 10:1 with dendritic cells ($1\text{-}5\times10^3$ cells) that were not treated with Picibanil (OK432) in IFN-γ capture antibody-coated plates in an incubator. Subsequent procedures followed the manual provided by the ELISPOT kit. That is, each well was washed with distilled water and a wash buffer, and a detection antibody was applied to the wells. Afterwards, the antibody was reacted for 1 hr with an enzyme-conjugated secondary antibody, followed by enzymatic reaction with a suitable substrate. After terminating the reaction, the reaction mixture was dried overnight, and the spots were counted using an ELISPOT reader (ImmunoSpot). The result is shown in FIG. 13.

After being reacted with target cells, the induced CTLs were measured for cytotoxicity. Cells that matched in HLA type with CTL and expressed the antigen (HepG2), cells that matched in HLA type with CTL but did not expressed the antigen (Hep3B), and cells that matched neither HLA type nor expressed the antigen (SN12C) were used as the target cells for killing assay. One day before the CTL activity test, the target cells were seeded at a density of $1\times10^4$ cells/well in 96-well flat bottomed plates. The activated T cells were added at predetermined ratios to the target cells and they were co-cultured for 18~24 hrs. After being fixed in 10% formalin for 1 hr, the cells were stained for 30 min with 0.4% crystal violet and then added with 80% methanol. Absorbance at 570 nm was read to evaluate cytotoxicity. The result is given in FIG. 14.

Figure 14:
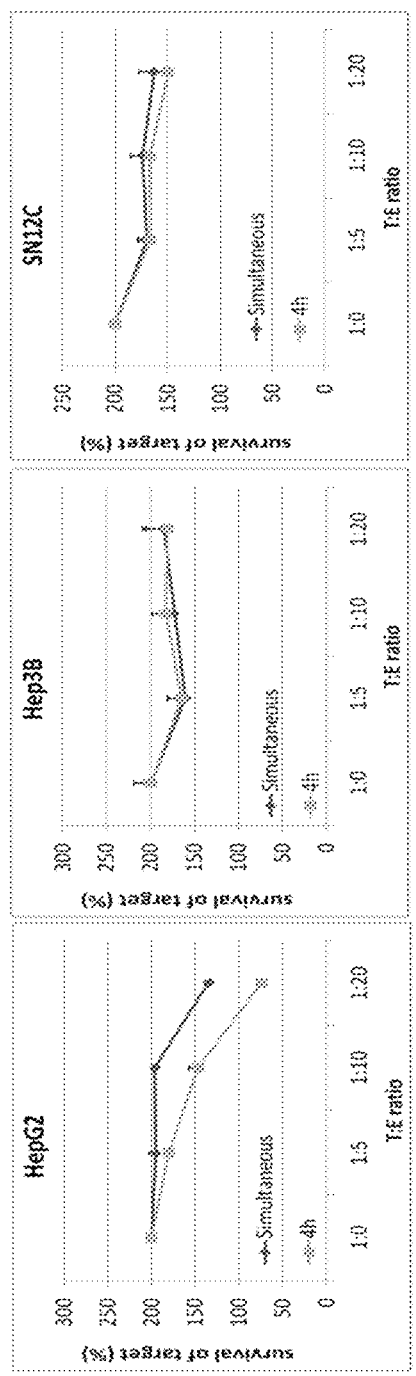
FIG. 14 shows antigen-specific cytotoxicity of the CTL of Example 1-3 (GPC-3/OK+) and Example 2-3 (GPC-3/OK+).

As can be seen, higher antigen specificity was detected in the group that was treated with Picibanil (OK432) 4 hrs after antigen treatment (Example 2-3) than in the group in which simultaneous treatment was performed (Example 1-3) (FIG. 13), and higher cytotoxicity was also obtained in the group in which treatment was performed with a time lag (4 hrs) (FIG. 14).

Experimental Example 5

Effect of Treatment with Antigen and Picibanil (OK432) at Time Lag

Cells of Examples 3-1 to 3-5 in which maturation was induced with Picibanil (OK432) at different times after pulsing with the antigen AFP, GPC-3 or MAGE-1 were assayed for the immunity induction of dendritic cells and the antigen-specific immune response of CTL.

Figure 15:
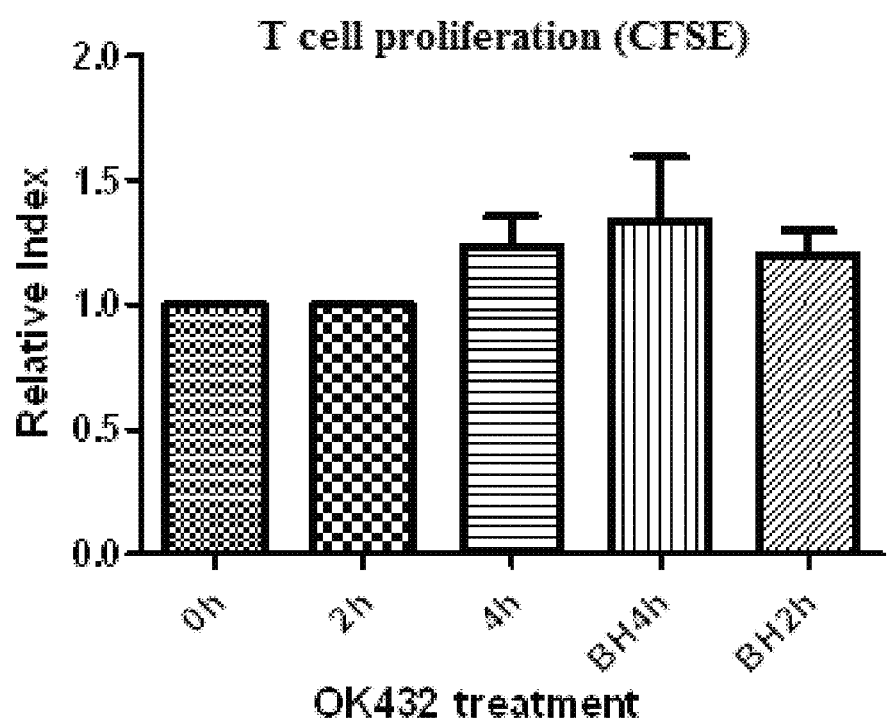
FIG. 15 is a graph showing T cell proliferation induced by dendritic cells of Examples 3-1 to 3-5.

First, isolated autologous T cells were suspended at a total population of $5\times10^6$ cells in 2 mL of a culture medium, and CFSE (carboxyfluorescein diacetate, succinimidyl ester) was added at a final concentration of 5-25 μM to the cell suspension. And they were incubated for 15 min at 37° C. in an incubator. After two rounds of washing with the culture medium, the cells were counted, and added at a density of $1\times10^5$ cells/well. The cells were co-cultured with $1\times10^4$ dendritic cells for 5 days. Thereafter, cells were stained with fluorescent-labeled anti-CD3 antibody, and analyzed by flow cytometry (FACS) to calculate T cell fractions) ($CD3^+$ $CFSE^{lo}$). The results are depicted in FIG. 15 by collecting each result for antigens AFP, GPC-3 and MAGE-1.

Figure 16:
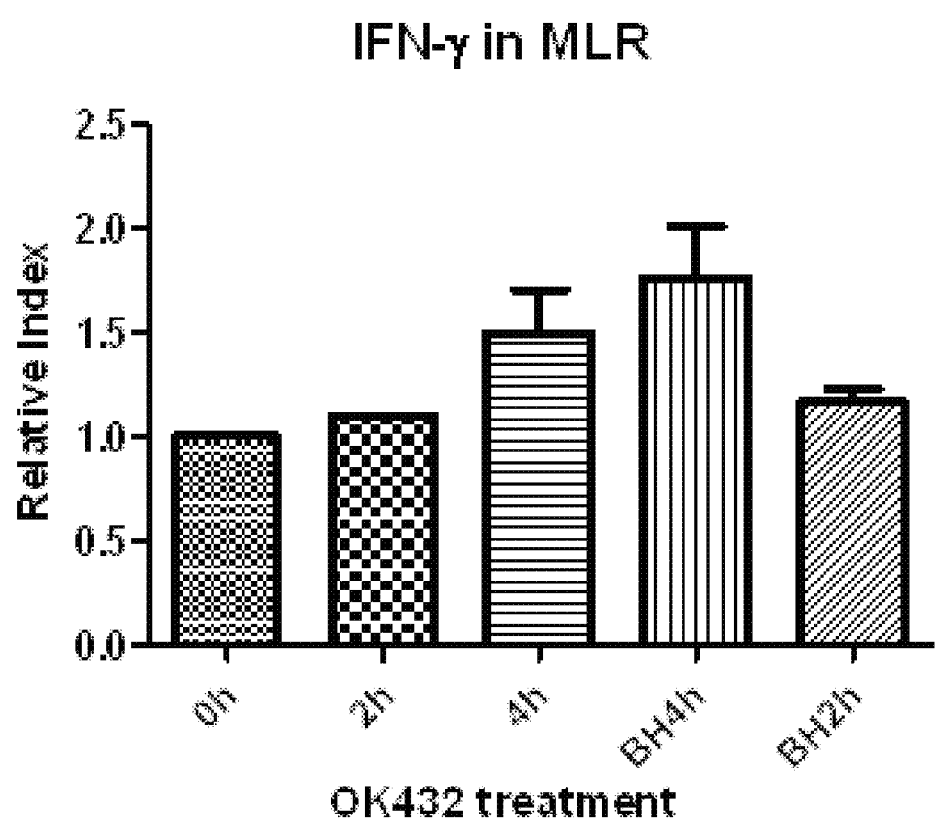
FIG. 16 is graph showing Th1 immune responses induced by dendritic cells of Examples 3-1 to 3-5.

In addition, the isolated autologous T cells were mixed at a ratio of 10:1 with the dendritic cells and cultured for 5 days, and the cell cultures were assayed for IFN-γ level using ELISA and re-calculated as a relative index. The results are depicted in FIG. 16 by collecting each result for antigens AFP, GPC-3 and MAGE-1.

Figure 17:
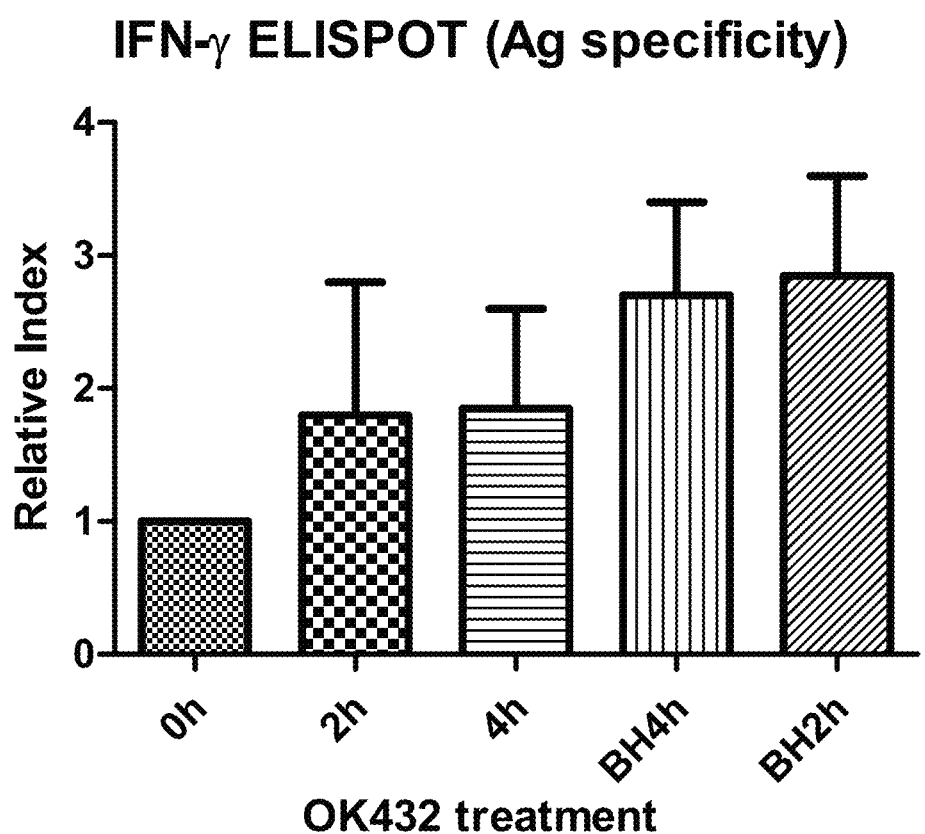
FIG. 17 is graph showing antigen specificity of the CTL induced by dendritic cells of Examples 3-1 to 3-5, as measured by IFN-γ ELISPOT analysis.

The induced CTL was reacted at a ratio of 10:1 with the dendritic cells of Comparative Example 3 for 18~20 hrs, and IFN-γ producing cells were analyzed by ELISPOT assay and re-calculated as a relative index. The results are depicted in FIG. 17 by collecting each result for antigens AFP, GPC-3 and MAGE-1.

As is understood from the data, the group that was treated with Picibanil (OK432) 4 hrs after antigen pulsing was superior in killing activity and antigen specificity, as demonstrated by IFN-γ ELISPOT assay, etc.

In addition to enhancing the ability of dendritic cells to induce an immune response, the composition of the maturation composition of the present invention can increase antigen-specific T cell immune responses, with the concomitant decrease of non-specific immune responses, thereby bringing about a maximal immunotherapeutic effect.

What is claimed is:

1. A method for preparing antigen-specific dendritic cells comprising:
    (a) pulsing immature dendritic cells with an antigen;
    (b) maturing the dendritic cells by treating the dendritic cells with at least one maturation factor selected from the group consisting of Interleukin-1β (IL-1β), Interleukin-6 (IL-6), Tumor necrosis factor-α (TNF-α), Interferon gamma (IFN-γ), Prostaglandin E2 (PGE2), and Poly IC; and
    (c) maturing the dendritic cells by treating the dendritic cells with Picibanil (OK432) 4 to 30 hours after steps (a) and (b).

2. The method of claim 1, wherein the antigen is at least one selected from the group consisting of a lysate of cancer cell line or cancer tissue, AFP (Alpha-fetoprotein), GPC-3 (Glypican-3), PSA (Prostate specific antigen), MAGE-1 (Melanoma-associated antigen 1), PSMA (Prostate-specific membrane antigen), PAP (Prostatic acid phosphatase), and a recombinant protein thereof.

3. The method of claim 1, further comprising (d) harvesting mature dendritic cells, wherein the dendritic cells are treated with Picibanil 5 hours before the mature dendritic cells are harvested.

4. The method of claim 1, further comprising (d) harvesting mature dendritic cells, wherein the dendritic cells are treated with Picibanil 4 hours before the mature dendritic cells are harvested.

* * * * *